United States Patent [19]

Derungs

[11] 4,382,945

[45] May 10, 1983

[54] TETRAHYDROTHIEPINO[4,5-d]IMIDAZOLE DERIVATIVES, COMPOSITION AND METHOD OF USE

[75] Inventor: Romano Derungs, Riehen, Switzerland

[73] Assignee: Hoffmann-La Roche Inc., Nutley, N.J.

[21] Appl. No.: 254,826

[22] Filed: Apr. 16, 1981

[30] Foreign Application Priority Data

Apr. 29, 1980 [CH] Switzerland .................. 3304/80
Feb. 16, 1981 [CH] Switzerland .................. 1057/81

[51] Int. Cl.³ ............... A61K 31/415; C07D 495/04
[52] U.S. Cl. .................... 424/273 R; 548/323
[58] Field of Search ............... 548/323; 424/273 R

[56] References Cited

U.S. PATENT DOCUMENTS 3,185,691  5/1965  Pribyl et al. ............... 544/253
3,615,607  3/1967  Soma et al. ............... 430/606

FOREIGN PATENT DOCUMENTS 686524   3/1967  Belgium .
775028   5/1972  Belgium .
2132079  1/1973  Fed. Rep. of Germany .
2262187  6/1974  Fed. Rep. of Germany .
2701372  7/1978  Fed. Rep. of Germany .
99787    8/1973  German Democratic Rep. .
39-19456 9/1964  Japan .
40-20706 9/1965  Japan .
43-26504 11/1968 Japan .

OTHER PUBLICATIONS

De Groot et al., J. Org. Chem. 1966, vol. 31(12), pp. 3954–3958.
Wynberg et al., Chem. Abst. 1965, vol. 63, p. 5630e.
Corvers et al., Chem. Abst. 1974, vol. 80, No. 95830j.
Wynberg et al., Chem. Commun. 1965, No. 9, p. 171.

Primary Examiner—John M. Ford
Assistant Examiner—Natalia Harkaway
Attorney, Agent, or Firm—Jon S. Saxe; Bernard S. Leon; William G. Isgro

[57] ABSTRACT

Imidazole derivatives of the formula

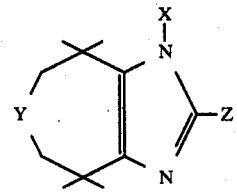

wherein X is hydrogen or $C_{1-4}$-alkyl, Y is sulfur, sulfinyl or sulfonyl and Z is thienyl, optionally substituted by methyl or fluorine, or a group of the formula

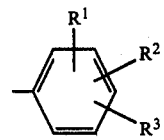

wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono- or di-($C_{1-4}$-alkyl)-amino and the other two are hydrogen, and physiologically or pharmaceutically compatible or acceptable acid addition salts thereof, are described. The compounds of formula I inhibit the aggregation of the blood platelets and have antihyperglycemic activity.

9 Claims, No Drawings

TETRAHYDROTHIEPINO[4,5-D]IMIDAZOLE DERIVATIVES, COMPOSITION AND METHOD OF USE

BRIEF SUMMARY OF THE INVENTION

The invention relates to imidazole derivatives of the formula

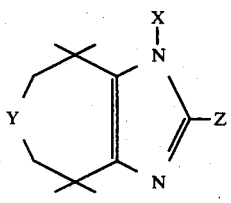

I wherein x is hydrogen or $C_{1-4}$-alkyl, Y is sulfur, sulfinyl or sulfonyl and Z is thienyl, optionally substituted by methyl or fluorine, or a group of the formula

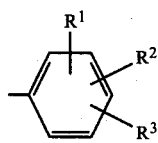

Z wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono- or di-($C_{1-4}$-alkyl)-amino and the other two are hydrogen,
and physiologically or pharmaceutically compatible or acceptable acid addition salts thereof, are described.

DETAILED DESCRIPTION OF THE INVENTION

The invention relates to imidazole derivatives of the formula

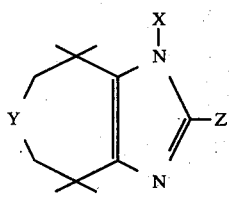

I wherein X is hydrogen or $C_{1-4}$-alkyl, Y is sulfur, sulfinyl or sulfonyl and Z is thienyl, optionally substituted by methyl or fluorine, or a group of the formula

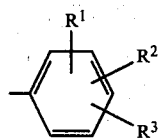

Z wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono-or di-($C_{1-4}$-alkyl)-amino and the other two are hydrogen,
and physiologically or pharmaceutically compatible or acceptable acid addition salts thereof, especially mineral acid salts thereof.

As used herein, the expression $C_{1-4}$-alkyl denotes straight-chain alkyl groups, i.e., methyl, ethyl, n-propyl and n-butyl.

Among the compounds of formula I, those wherein X is hydrogen and/or Y is sulfur and/or Z is phenyl, p-(fluoro or methoxy)-phenyl 3,4,5-trimethoxyphenyl, 3,4-methylenedioxyphenyl or 2-thienyl are preferred.

2-Phenyl-4,5,7,8-tetrahydro-4,4,8,8-tetramethyl-1-H-thiepino[4,5-d]imidazole and 2-(p-fluorophenyl)-4,5,7,8-tetrahydro-4,4,8,8-tetramethyl-1-H-thiepino[4,5-d]imidazole are especially preferred.

The invention also relates to a process for the preparation of the aforementioned compounds as well as pharmaceutical preparations based on the compounds of formula I.

Examplary of physiologically compatible or pharmaceutically acceptable mineral acid salts are hydrochlorides, hydrobromides, sulfates, phosphates and the like.

The aforementioned compounds of formula I and their salts can be prepared in accordance with the invention as follows. To prepare a compound of formula I wherein X is hydrogen, a diketone of the formula

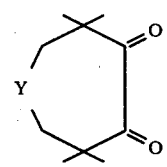

II wherein Y is as previously described,
is reacted with an aldehyde of the formula

Z—CH=O    III wherein Z is as previously described,
in the presence of a polar solvent containing ammonium ions.

To prepare a compound of formula I wherein X is $C_{1-4}$-alkyl, a compound of formula I wherein X is hydrogen is alkylated; if desired, a compound of formula I wherein y is sulfur is oxidized to give a compound of formula I wherein Y is sulfinyl, and, if desired, a compound of formula I is converted into a physiologically compatible or pharmaceutically acceptable acid addition salt.

As the source of ammonium ions there are conveniently used ammonium salts, preferably of carboxylic acids, such as, ammonium acetate. Examples of polar solvents are dimethyl sulfoxide and dimethyformamide. The reaction of the diketone II with the aldehyde III is conveniently carried out with heating to the reflux temperature, preferably at a range of from 50° to 120° C., especially at a range of from 90° to 100° C.

In place of the diketone II there can be used as the starting material the corresponding α-ketol. In this case the reaction must be carried out in the presence of an oxidizing agent, such as, copper (II) acetate or lead (IV) acetate.

The alkylation of a N-unsubstituted compound I can be carried out by reacting the latter with an alkali metal hydride, for example, sodium hydride, in an anhydrous solvent such as dimethylformamide, and reacting the compound obtained with an alkyl halide, for example, methyl iodide.

The conversion of a compound of formula I, wherein Y is sulfur, into the corresponding sulfoxide can be carried out with an oxidizing agent such as sodium periodate, in a solvent such as aqueous methanol, conveniently at a low temperature, preferably at a temperature in the range of from about 0° to 5° C.

The compounds of formula I and the physiologically compatible or pharmaceutically acceptable acid addition salts thereof can be used as medicaments. They inhibit the aggregation of the blood platelets and have antihyperglycemic activity. Therefore, they can be used for the prophylaxis of thromboses or for the treatment of diabetes.

The compounds of formula I can be used as medicaments, for example, in the form of pharmaceutical preparations which contain them or their salts in admixture with a pharmaceutical organic or inorganic inert carrier material which is suitable for enteral or parenteral administration such as, for example, water, gelatin, gum arabic, lactose, starch, magnesium stearate, talc, vegetable oils, polyalkyleneglycols or the like. The pharmaceutical preparations can be made up in solid form, for example, as tablets, dragées, suppositories, or capsules, or in liquid form, for example, as solutions, suspensions or emulsions. The pharmaceutical preparations can be sterilized and/or can contain adjuvants such as preserving, stabilizing, wetting or emulsifying agents, salts for varying the osmotic pressure or buffers. They can also contain still other therapeutically valuable substances. The oral administration of the compounds of formula I of the invention is preferred. For adults there come into consideration an oral daily dosage in the range of 0.5 to 30 mg/kg and a parenteral daily dosage in the range of 0.05 to 10 mg/kg.

The aggregation-inhibiting activity was demonstrated according to the aggregometer method of BORN (Nature 194, 927 (1962)] and MICHAL and BORN (Nature 231, 220 (1971)]. The maximum aggregation velocity was taken as the test parameter and the effective concentration ($EC_{50}$) was ascertained from dose-activity curves.

Human platelet-rich plasma was obtained by centrifugation from citrated venous blood. The experiments were carried out with suspensions of the test substances in 0.9% sodium chloride. 0.18 ml of citrate plasma were treated with a 10 μl suspension of the test compounds and incubated at 37° C. for 10 minutes, whereupon the aggregation was initiated by the addition of 10 μl of a suspension of collagen-fibrils.

The results are reproduced in Table I.

TABLE I

| Collagen-induced blood platelet aggregation | |
|---|---|
| Compound | $EC_{50}$ (μM) |
| 2-Phenyl-4,5,7,8-tetrahydro-4,4,8,8-tetramethyl-1-H-thiepino[4,5-d]imidazole hydrochloride | 0.8 |
| 2-(3,4-Methylenedioxyphenyl)-4,5,7,8-tetrahydro-4,4,8,8-tetramethyl-1-H-thiepino[4,5-d]imidazole hydrochloride | 1.2 |
| 2-(p-Methoxyphenyl)-4,5,7,8-tetrahydro-4,4,8,8-tetramethyl-1-H-thiepino[4,5-d]imidazole hydrochloride | 4.2 |
| 4,5,7,8-Tetrahydro-4,4,8,8-tetramethyl-2-(2-thienyl)-1-H-thiepino[4,5-d]imidazole hydrochloride | 19.7 |
| 2-(p-Fluorophenyl)-4,5,7,8-tetrahydro-4,4,8,8-tetramethyl-1-H-thiepino[4,5-d]imidazole hydrochloride | 4.7 |

The antihyperglycemic activity can be demonstrated as follows:

Gum arabic (12 control animals) or 0.3 mmol/kg p.o. of test substance (6 experimental animals) is administered to rats (fasted for 24 hours) and 100 minutes later a suspension of 1.6 g of glucose in 10 ml of 5 percent gum arabic is administered orally per kg body weight. The animals are killed 20 minutes after the glucose administration. Plasma is obtained from the heparinized mixed blood. The glucose concentration in the plasma is determined according to the hexokinase method. The averages of the glucose concentration, expressed in percentages of the controls, are given in Table II.

TABLE II

| Plasma glucose concentration | |
|---|---|
| Compound | Glucose concentration (%) |
| 2-Phenyl-4,5,7,8-tetrahydro-4,4,8,8-tetramethyl-1-H-thiepino[4,5-d]imidazole | 74 |
| 2-Phenyl-4,5,7,8-tetrahydro-4,4,8,8-tetramethyl-1-H-thiepino-8 4,5-d]imidazole hydrochloride | 67 |
| 2-(p-Fluorophenyl)-4,5,7,8-tetrahydro-4,4,8,8-tetramethyl-1-H-thiepino[4,5-d]imidazole hydrochloride | 77 |

The Examples which follow further illustrate the invention. All temperatures are in degrees Centigrade unless otherwise stated.

EXAMPLE 1

Preparation of 2-phenyl-4,5,7,8-tetrahydro-4,4,8,8-tetramethyl-1-H-thiepino[4,5-d]imidazole 16 g of 3,3,6,6-tetramethyl-4,5-thiepanedione and 8 g of benzaldehyde are dissolved in 200 ml of dimethyl sulfoxide, 60 g of anhydrous ammonium acetate are added thereto with stirring and the mixture is heated at 90° C.

After cooling, the reaction mixture is poured into ice-water with stirring, the solution is made alkaline with concentrated sodium hydroxide and extracted with ether. The organic phase is washed with ice-water and concentrated to dryness. The residue is covered with petroleum ether and rubbed with a glass rod. The precipitate removed by filtration is recrystallized from toluene, and there is obtained 2-phenyl-4,5,7,8-tetrahydro-4,4,8,8-tetramethyl-1-H-thiepino[4,5-d]imidazole, m.p. 225°–227° C.

To prepare the hydrochloride salt 500 mg of the base are dissolved in 50 ml of ether and ethereal hydrochloric acid is added dropwise thereto with stirring until product no longer separates out. The precipitate is removed by filtration and washed with ether and ethanol. After filtration and drying, there are obtained 600 mg of the hyrochloride salt, m.p. 300° C.

EXAMPLE 2

Preparation of
2-(3,4-Methylenedioxyphenyl)-4,5,7,8-tetrahydro-4,4,8,8-tetramethyl-1-H-thiepino[4,5-d]imidazole The following compound is prepared in a manner analogous to Example 1.

2-(3,4-Methylenedioxyphenyl)-4,5,7,8-tetrahydro-4,4,8,8-tetramethyl-1-H-thiepino[4,5-d]imidazole, m.p. 179°–180° C.; m.p. of the hydrochloride; 270° C. (decomposition).

EXAMPLE 3

Preparation of
2-(p-methoxyphenyl)-4-5-7-8-tetrahydro-4,4,8,8-tetramethyl-1-H-thiepino[4,5-d]imidazole 4 g of 3,3,6,6-tetramethyl-4,5-thiepanedione, 2.72 g of anisaldehyde and 15 g of anhydrous ammonium acetate are dissolved in 50 ml of dimethyl sulfoxide. The reaction is carried out for 4 hours at 95° C. with stirring.

The reaction mixture is poured into ice-water and the mixture is made alkaline with ammonia. It is then extracted with ether. The combined extracts are washed with water, dried and freed from solvent. The residue is dissolved in ether and treated with petroleum ether until turbidity begins. After the product has crystallized out, the crystals are removed by filtration and washed with ether. After recrystallization from n-heptane, there is obtained 2-(p-methoxyphenyl-4-5-7-8-tetrahydro-4,4,8,8-tetramethyl-1-H-thiepino[4,5-d]imidazole, m.p. 175°–176° C.; m.p. of the hydrochloride: 250° C. (decomposition).

EXAMPLE 4

The following compounds are prepared in a manner analogous to Example 3:

2-(m-Methoxyphenyl)-4,5,7,8-tetrahydro-4,4,8,8-tetramethyl-1-H-thiepino[4,5-d]imidazole, m.p. 185°–187° C.; m.p. of the hydrochloride: 280° C. (decomposition), 2-(o-methoxyphenyl)-4,5,7,8-tetrahydro-4,4,8,8-tetramethyl-1-H-thiepino[4,5-d]imidazole, m.p. 140°–141° C.; m.p. of the hydrochloride: 245° C. (decomposition), 4,5,7,8-tetrahydro-4,4,8,8-tetramethyl-2-(p-tolyl)-1-H-thiepino[4,5-d]imidazole, m.p. 211°–213° C.; m.p. of the hydrochloride: 270°–275° C., 4,5,7,8-tetrahydro-4,4,8,8-tetramethyl-2-(m-tolyl)-1-H-thiepino[4,5-d]imidazole, m.p. 237°–240° C.; m.p. of the hydrochloride: 260° C. (decomposition), 2-(p-methylthiophenyl)-4,5,7,8-tetrahydro-4,4,8,8-tetramethyl-1-H-thiepino[4,5-d]imidazole, m.p. 165°–167° C.; m.p. of the hydrochloride: 270°–280° C. (decomposition), 4,5,7,8-tetrahydro-4,4,8,8-tetramethyl-2-(o-tolyl)-1-H-thiepino[4,5-d]imidazole, m.p. 110°–115° C.; m.p. of the hydrochloride: 275° C. (decomposition), p-(4,5,7,8-tetrahydro-4,4,8,8-tetramethyl-1-H-thiepino[4,5-d]imidazol-2-yl)-phenol, m.p. 255° C.; m.p. of the hydrochloride: 300° C. (decomposition), m-(4,5,7,8-tetrahydro-4,4,8,8-tetramethyl-1H-thiepino[4,5-d]imidazol-2-yl)-phenol, m.p. 118°–120° C.; m.p. of the hydrochloride: 300° C. (decomposition), o-(4,5,7,8-tetrahydro-4,4,8,8-tetramethyl-1-H-thiepino[4,5-d]imidazol-2-yl)-phenol, m.p. 204°–206° C.; m.p. of the hydrochloride: 250° C. (decomposition), 2-(4,6-dimethylphenyl)-4,5,7,8-tetrahydro-4,4,8,8-tetramethyl-1-H-thiepino[4,5-d]imidazole, m.p. 142°–144° C.; m.p. of the hydrochloride: 310° C. (decomposition), 2-(3,4-dimethylphenyl)-4,5,7,8-tetrahydro-4,4,8,8-tetramethyl-1-H-thiepino[4,5-d]imidazole, m.p. 218°–220° C.; m.p. of the hydrochloride: 275° C. (decomposition), 2-(3,4-dimethoxyphenyl)-4,5,7,8-tetrahydro-4,4,8,8-tetramethyl-1-H-thiepino[4,5-d]imidazole, m.p. 138°–140° C.; m.p. of the hydrochloride: 140° C. (decomposition), 4,5,7,8-tetrahydro-4,4,8,8-tetramethyl-2-(2,4,5-trimethoxyphenyl)-1-H-thiepino[4,5-d]imidazole, m.p. 141°–143° C.; m.p. of the hydrochloride: 218°–220° C., 4,5,7,8-tetrahydro-4,4,8,8-tetramethyl-2-(2,4,6-trimethoxyphenyl)-1-H-thiepino[4,5-d]imidazole, m.p. 141°–142° C.; m.p. of the hydrochloride: 235°–240° C. (decomposition), 4,5,7,8-tetrahydro-4,4,8,8-tetramethyl-2-(3,4,5-trimethoxyphenyl)-1-H-thiepino[4,5-d]imidazole, m.p. 188°–190° C.; m.p. of the hydrochloride: 290° C. (decomposition), 2-(3,4-ethylenedioxyphenyl)-4,5,7,8-tetrahydro-4,4,8,8-tetramethyl-1-H-thiepino[4,5-d]imidazole, m.p. 178°–180° C., m.p. of the hydrochloride: 195° C. (decomposition), 2-[p-(diethylamino)-phenyl]-4,5,7,8-tetrahydro-4,4,8,8-tetramethyl-1-H-thiepino[4,5-d]imidazole, m.p. 190°–102° C., m.p. of the hydrochloride: 250° C. (decomposition), 4,5,7,8-tetrahydro-4,4,8,8-tetramethyl-2-(2-thienyl)-1-H-thiepino[4,5-d]imidazole, m.p. 213°–215° C., m.p. of the hydrochloride: 250° C. (decomposition), 2-(m-fluorophenyl)-4,5,7,8-tetrahydro-4,4,8,8-tetramethyl-1-H-thiepino[4,5-d]imidazole, m.p. 199°–200° C., m.p. of the hydrochloride: 290° C. (decomposition), 2-(o-fluorophenyl)-4,5,7,8-tetrahydro-4,4,8,8-tetramethyl-1-H-thiepino[4,5-d]imidazole, m.p. 98°–99° C., m.p. of the hydrochloride: 300° C. (decomposition), 2-(p-fluorophenyl)-4,5,7,8-tetrahydro-4,4,8,8-tetramethyl-1-H-thiepino[4,5-d]imidazole, m.p. 195°–198° C., m.p. of the hydrochloride: 300° C. (decomposition).

EXAMPLE 5

Preparation of
2-(5-methoxy-3,4-methylenedioxyphenyl)-4,5,7,8-tetrahydro-4,4,8,9-tetramethyl-1-H-thiepino[4,5-d]imidazole 4 g of 3,3,6,6-tetramethyl-4,5-thiepanedione and 3.6 g of 3,4-methylenedioxy-5-methoxybenzaldehyde are dissolved in 50 ml of dimethylformamide. 15.5 g of anhydrous ammonium acetate are then added thereto. The reaction is carried out with stirring for 5 hours at 95° C.

After cooling, the reaction mixture is poured into ice-water while stirring. The mixture is made alkaline with ammonia and then extracted with ether. The organic phase is washed with water, dried and concentrated. The crystalline residue is triturated with ether and petroleum ether and removed by filtration under suction. After recrystallization from n-heptane, there is obtained 2-(5-methoxy-3,4-methylenedioxyphenyl)-

4,5,7,8-tetrahydro-4,4,8,8-tetramethyl-1-H-thiepino[4,5-d]imidazole, m.p. 175°–178° C.; m.p. of the hydrochloride: 300° C. (decomposition).

EXAMPLE 6

Preparation of
2-phenyl-4,5,7,8-tetrahydro-4,4,8,8-tetramethyl-1-H-thiepino-[4,5-d]imidazole 6,6-dioxide 1.5 g of 3,3,6,6-tetramethyl-4,5-thiepanedione 1,1-dioxide, 7 g of benzaldehyde and 5 g of anhydrous ammonium acetate are dissolved in 16 ml of dimethyl sulfoxide. The reaction mixture is heated to 95° C. while stirring and subsequently left to react under the same conditions for an additional 4 hours. At room temperature, the mixture is then poured into ice-water with stirring, made alkaline with concentrated sodium hydroxide and extracted with ethyl acetate. The organic phase is washed with icewater and dried. The solvent is removed by distillation. The residue is treated with ether, the product crystallizing out. For the recrystallization, it is dissolved in ethyl acetate and, after filtration, treated with n-hexane, whereby there is obtained 2-phenyl-4,5,7,8-tetrahydro-4,4,8,8-tetramethyl-1-H-thiepino[4,5-d]imidazole 6,6-dioxide, m.p. 260°–263° C.; m.p. of the hydrochloride: 300° C.

EXAMPLE 7

Preparation of
2-(m-Methoxyphenyl)-4,5,7,8-tetrahydro-4,4,8,8-tetramethyl-1-H-thiepino[4,5-d]imidazole 6,6-dioxide 2-(m-Methoxyphenyl)-4,5,7,8-tetrahydro-4,4,8,8-tetramethyl-1-H-thiepino[4,5-d]imidazole 6,6-dioxide, m.p. 217°–219° C., is prepared in a manner analogous to Example 6.

EXAMPLE 8

Preparation of
2-phenyl-4,5,7,8-tetrahydro-4,4,8,8-tetramethyl-1-H-thiepino[4,5-d]imidazole 4.04 g of 5-hydroxy-2,3,6,7-tetrahydro-3,3,6,6-tetramethyl-4(5H)-thiepinone are dissolved in 100 ml of methanol with stirring at 50° C. 5 g of copper (II) acetate monohydrate are added, followed by 2.12 g of benzaldehyde. Then, 60 ml of concentrated aqueous ammonia solution are added dropwise. Thereafter, the mixture is boiled at reflux for 4 hours and subsequently filtered while hot. The filter cake is flushed with hot methanol and dried by suction.

The copper salt precipitate is suspended in aqueous ethanol and made acid with 2 N hydrochloric acid. Hydrogen sulfide is then conducted in at 80° C. with stirring. After 3 hours, the copper sulfide is removed by filtration. The filtrate is concentrated, and the suspension is made alkaline with concentrated ammonia and extracted with ether. After drying the organic phase and concentration, the residue is recrystallized from n-heptane and there is obtained 2-phenyl-4,5,7,8-tetrahydro-4,4,8,8-tetramethyl-1-H-thiepino[4,5-d]-imidazole, m.p. 223°–224° C.

EXAMPLE 9

Preparation of
2-phenyl-4,5,7,8-tetrahydro-4,4,8,8-tetramethyl-1-H-thiepino-[4,5-d]-imidazole 6-oxide 1.43 g of 2-phenyl-4,5,7,8-tetrahydro-4,4,8,8-tetramethyl-1-H-thiepino[4,5-d]imidazole are dissolved in 75 ml of methanol and cooled to 2° C. with stirring. The solution is treated dropwise at this temperature with a solution of 1.3 g of sodium periodate in 28 ml of water. The mixture is left to react-out at the same temperature for 3 hours. Thereupon, 25 ml of methanol are added. After stirring for 5 hours at room temperature, the solution is concentrated. The product is left to crystallize-out while cooling with ice. The precipitate is removed by filtration and the crystals are covered with acetone and ether. After filtration, the 2-phenyl-4,5,7,8-tetrahydro-4,4,8,8-tetramethyl-1-H-thiepino-[4,5-d]-imidazole 6-oxide is recrystallized from ethanol/n-hexane, m.p. 273°–275° C.; m.p. of the hydrochloride: 300° C.

EXAMPLE 10

Preparation of
2-(m-methoxyphenyl)-4,5,7,8-tetrahydro-4,4,8,8-tetramethyl-1-H-thiepino[4,5-d]imidazole 6-oxide 2-(m-Methoxyphenyl)-4,5,7,8-tetrahydro-4,4,8,8-tetramethyl-1-H-thiepino[4,5-d]imidazole 6-oxide
2(m-Methoxyphenyl)-4,5,7,8-tetrahydro-4,4,8,8tetramethyl-1H-thiepino[4,5d]imidazole 6-oxide, m.p. 205°–207° C., is prepared in a manner analogous to Example 9.

EXAMPLE 11

Preparation of
2-phenyl-4,5,7,8-tetrahydro-1,4,4,8,8-pentamethyl-1-H-thiepino[4,5-d]imidazole A suspension of 0.44 g of sodium hydride (55% in paraffin) in 10 ml of dimethylformamide is cooled to 0° C. under nitrogen or argon. Thereupon, there is added dropwise a solution of 2.86 g of 2-phenyl-4,5,7,8-tetrahydro-4,4,8,8-tetramethyl-1-H-thiepino[4,5-d]imidazole dissolved in 10 ml of dimethylformamide. The mixture is then left to react at room temperature for 20 minutes. Thereafter, 2.1 g of methyl iodide in 10 ml of dimethylformamide are added dropwise. The mixture is left to react at room temperature for an additional 30 minutes.

The reaction mixture is poured into ice-water with stirring. The precipitate is removed by filtration and washed in water. The filter residue is dissolved in ether and the solution is dried and concentrated. The suspension is treated with petroleum ether. After crystallization, the mixture is filtered and the product is recrystallized from n-heptane. The 2-phenyl-4,5,7,8-tetrahydro-1,4,4,8,8-pentamethyl-1-H-thiepino [4,5-d]imidazole which is obtained melts at 158°–160° C. M.p. of the hydrochloride: 240° C. (decomposition).

EXAMPLE 12

The following compounds are prepared in a manner analogous to Example 11:
2-Phenyl-4,5,7,8-tetrahydro-1,4,4,8,8-pentamethyl-1-H-thiepino[4,5-d]imidazole 6-oxide, m.p. 178°–180° C.; m.p. of the hydrochloride: 170° C. (decomposition),
1-(n-butyl)-2-phenyl-4,5,7,8-tetrahydro-4,4,8,8-tetramethyl-1-H-thiepino[4,5-d]imidazole, m.p. 100° C.; m.p. of the hydrochloride: 120° C. (decomposition).

EXAMPLE 13

Tablets of the following composition are prepared in the usual manner:

---

2-p-Fluorophenyl-4,5,7,8-tetrahydro-
4,4,8,8-tetramethyl-1-H-thiepino-

-continued

| | |
|---|---|
| [4,5-d]imidazole hydrochloride | 185.0 mg |
| Lactose | 15.0 mg |
| Maize starch | 37.9 mg |
| Water-soluble polyvinylpyrrolidone | 10.0 mg |
| Magnesium stearate | 2.5 mg |
| Total weight per tablet | 250.0 mg |

EXAMPLE 14

Interlocking gelatin capsules of the following composition are prepared in the usual manner:

| | |
|---|---|
| 2-p-Fluorophenyl-4,5,7,8-tetrahydro-4,4,8,8-tetramethyl-1-H-thiepino-[4,5-d]imidazole hydrochloride | 200.0 mg |
| Water-soluble polyvinylpyrrolidone | 2.0 mg |
| Maize starch | 43.0 mg |
| Talc | 4.5 mg |
| Magnesium stearate | 0.5 mg |
| Total weight per capsule | 250.0 mg |

EXAMPLE 15

An injection solution of the following composition is prepared in the usual manner:

| | |
|---|---|
| 2-p-Fluorophenyl-4,5,7,8-tetrahydro-4,4,8,8-tetramethyl-1-H-thiepino-[4,5-d]imidazole hydrochloride | 115.0 mg |
| Glycerinformal | 2.4 ml |
| Water | 4.0 ml |

I claim:
1. A compound of the formula

$$\text{I}$$

wherein X is hydrogen or $C_{1-4}$-alkyl, Y is sulfur, sulfinyl or sulfonyl and Z is a group of the formula $$Z$$

wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono-or di-($C_{1-4}$-alkyl)-amino and the other two are hydrogen,
or physiologically compatible acid addition salt thereof.

2. A compound in accordance with claim 1, wherein X is hydrogen.

3. A compound in accordance with claim 2, wherein Y is sulfur.

4. A compound in accordance with claim 3 wherein Z is phenyl, p-(fluoro or methoxy)-phenyl, 3,4,5-trimethoxyphenyl, or 3,4-methylenedioxyphenyl.

5. A compound in accordance with claim 1, 2-phenyl-4,5,7-8-tetrahydro-4,4,8,8-tetramethyl-1-H-thiepino[4,5-d]imidazole.

6. A compound in accordance with claim 1, 2-p-fluorophenyl-4,5,7,8-tetrahydro-4,4,8,8-tetramethyl-1-H-thiepino[4,5-d]imidazole.

7. A compound in accordance with claim 1, selected from the group consisting of 2-(3,4-methylenedioxyphenyl)-4,5,7,8-tetrahydro-4,4,8,8-tetramethyl-1-H-thiepino[4,5-d]imidazole, 2-(p-methoxyphenyl)-4,5,7,8-tetrahydro-4,4,8,8-tetramethyl-1-H-thiepino[4,5-d]imidazole, 2-(m-methoxyphenyl)-4,5,7,8-tetrahydro-4,4,8,8-tetramethyl-1-H-thiepino[4,5-d]imidazole, 2-(o-methoxyphenyl)-4,5,7,8-tetrahydro-4,4,8,8-tetramethyl-1-H-thiepino[4,5-d]imidazole, 4,5,7,8-tetrahydro-4,4,8,8-tetramethyl-2-(p-tolyl)-1H-thiepino[4,5-d]imidazole, 4,5,7,8-tetrahydro-4,4,8,8-tetramethyl-2-(m-tolyl)-1-H-thiepino[4,5-d]imidazole, 2-(p-methylthiophenyl)-4,5,7,8-tetrahydro-4,4,8,8-tetramethyl-1-H-thiepino[4,5-d]imidazole, 4,5,7,8-tetrahydro-4,4,8,8-tetramethyl-2-(o-tolyl)-1-H-thiepino[4,5-d]imidazole, p-(4,5,7,8-tetrahydro-4,4,8,8-tetramethyl-1-H-thiepino[4,5-d]imidazole-2-yl)-phenol, m-(4,5,7,8-tetrahydro-4,4,8,8-tetramethyl-1H-thiepino[4,5-d]-imidazol-2-yl)-phenol, o-(4,5,7,8-tetrahydro-4,4,8,8,-tetramethyl-1-H-thiepino[4,5-d]imidazol-2-yl)-phenol, 2-(4,6-dimethylphenyl)-4,5,7,8-tetrahydro-4,4,8,8-tetramethyl-1-H-thiepino[4,5-d]imidazole, 2-(3,4-dimethylphenyl)-4,5,7,8-tetrahydro-4,4,8,8-tetramethyl-1-H-thiepino[4,5-d]imidazole, 2-(3,4-dimethoxyphenyl)-4,5,7,8-tetrahydro-4,4,8,8-tetramethyl-1-H-thiepino[4,5-d]imidazole, 4,5,7,8-tetrahydro-4,4,8,8,-tetramethyl-2-(2,4,5-trimethoxyphenyl)-1-H-thiepino[4,5-d]imidazole, 4,5,7,8-tetrahydro-4,4,8,8-tetramethyl-2-(2,4,6-trimethoxyphenyl)-1-H-thiepino[4,5-d]imidazole, 4,5,7,8-tetrahydro-4,4,8,8-tetramethyl-2-(3,4,5-trimethoxyphenyl)-1-H-thiepino[4,5-d]imidazole, 2-(3,4-ethylenedioxyphenyl)-4,5,7,8-tetrahydro-4,4,8,8-tetramethyl-1-H-thiepino[4,5-d]imidazole, 2-[p-(diethylamino)-phenyl]-4,5,7,8-tetrahydro-4,4,8,8-tetramethyl-1-H-thiepino[4,5-d]imidazole, 2-(m-fluorophenyl)-4,5,7,8-tetrahydro-4,4,8,8-tetramethyl-1-H-thiepino[4,5-d]imidazole, 2-(p-fluorophenyl)-4,5,7,8-tetrahydro-4,4,8,8-tetramethyl-1-H-thiepino[4,5-d]imidazole, 2-(5-methoxy-3,4-methylene dioxyphenyl)-4,5,7,8-tetrahydro-4,4,8,8-tetramethyl-1-H-thiepino[4,5-d]imidazole, 2-phenyl-4,5,7,8-tetrahydro-4,4,8,8-tetramethyl-1-H-thiepino[4,5-d]imidazole 6,6-dioxide, 2-(m-methoxyphenyl)-4,5,7,8-tetrahydro-4,4,8,8-tetramethyl-1-H-thiepino[4,5-d]imidazole 6,6-dioxide, 2-phenyl-4,5,7,8-tetrahydro-4,4,8,8-tetramethyl-1-H-thiepino[4,5-d]imidazole 6-oxide, 2-(m-methoxyphenyl)-4,5,7,8-tetrahydro-4,4,8,8-tetramethyl-1-H-thiepino[4,5-d]imidazole 6-oxide, 2-phenyl-4,5,7,8-tetrahydro-1,4,4,8,8-pentamethyl-1-H-thiepino[4,5-d]imidazole, 2-phenyl-4,5,7,8-tetrahydro-1,4,4,8,8-pentamethyl-1-H-thiepino[4,5-d]imidazole 6-oxide and 1-(n-butyl)-2-phenyl-4,5,7,8-tetrahydro-4,4,8,8-tetramethyl-1-H-thiepino[4,5-d]imidazole.

8. A blood platelet aggregation-inhibiting composition comprising an effective amount of a compound of the formula

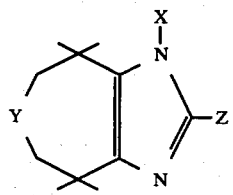

wherein X is hydrogen or $C_{1-4}$-alkyl, Y is sulfur, sulfinyl or sulfonyl and Z is a group of the formula

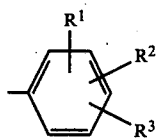

wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono-or di-($C_{1-4}$-alkyl)-amino and the other two are hydrogen, or physiologically compatible acid addition salt thereof, and a pharmaceutically inert carrier material.

9. A method of inhibiting blood platelet aggregation which comprises administering an effective amount of a compound of formula

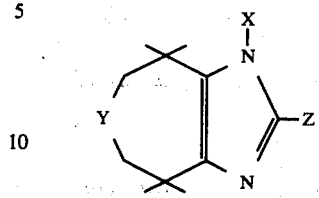

wherein X is hydrogen or $C_{1-4}$-alkyl, Y is sulfur, sulfinyl or sulfonyl and Z is a group of the formula

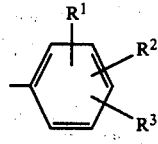

wherein $R^1$, $R^2$ and $R^3$ are hydrogen, methyl, fluorine, hydroxy, methoxy, methylthio or two of $R^1$, $R^2$ and $R^3$ on adjacent carbon atoms taken together are methylenedioxy or ethylenedioxy or one of $R^1$, $R^2$ and $R^3$ is mono-or di-($C_{1-4}$-alkyl)-amino and the other two are hydrogen, or physiologically compatible acid addition salt thereof.

* * * * *